(12) United States Patent
Yu

(10) Patent No.: US 7,682,827 B2
(45) Date of Patent: Mar. 23, 2010

(54) MICROELECTRONIC POSITIONING FOR BIOPARTICLES

(75) Inventor: Tung-Ming Yu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 321 days.

(21) Appl. No.: 11/316,819

(22) Filed: Dec. 27, 2005

(65) Prior Publication Data

US 2007/0077656 A1    Apr. 5, 2007

(30) Foreign Application Priority Data

Oct. 3, 2005    (TW) .............................. 94134479 A

(51) Int. Cl.
*C12N 13/00*    (2006.01)
(52) U.S. Cl. .................... 435/383; 435/173.9
(58) Field of Classification Search ........................ None
See application file for complete search history.

(56) References Cited

U.S. PATENT DOCUMENTS

| 5,795,457 | A | 8/1998 | Pethig et al. |
| 6,653,124 | B1 | 11/2003 | Freeman |
| 2004/0180330 | A1 | 9/2004 | Vesey |

FOREIGN PATENT DOCUMENTS

TW    200615536    11/1993

OTHER PUBLICATIONS

M. Ozkan, T. Pisanic, J. Scheel, C. Barlow S. Esener, and S. N. Bhatia, Electro-Optical Platform for the Manipulation of Live Cells, American Chemical Society, Oct. 2, 2002.

Tai HyunPark and Michael L. Shuler, Integration of Cell Culture and Microfabrication Technology, Biotechnol, Prog. 2003, 19, 243-253.

Jorge J. Capurro, et al. "Microchannel for Dielectrophoretic Separation of Bioparticles", Drexel University—Mechanical Engineering Department, Dec. 17, 2004, pp. 1-18.

K.V.I.S. Kaler, et al., "Bioparticle Mechatronics", Department of Electrical and Computer Engineering, Department of Chemistry, University of Calgary, Calgarly, Alt, Canada, 1996, pp. 100-103.

A.P. Brown et al. "Evaluation of a dielectrophoretic bacterial counting technique", Dec. 14, 1998, Abstract Biosens. Bioelectronics vol. 14, pp. 341-351.

Ying Huang et al. "Dielectrophoretic Cell Seperation and Gene Expression Profiling on Microelectronic Chip Arrays," Jul. 15, 2002, Analytical Chemistry, vol. 74, No. 14 p. 3362.

Chia-Fu Chou et al. "Electrodeless Dielectrophoresis of Single- and Doulbe-Stranded DNA," Oct. 2002, Biophysical Journal, vol. 83, p. 2170.

Michael P. Hughes et al. "Measuring the dielectric properties of herpes simplex virus type 1 virions with dielectrophoresis," Jan. 17, 2002, Abstract BBA 1571, pp. 1-8.

*Primary Examiner*—James S Ketter
(74) *Attorney, Agent, or Firm*—Bacon & Thomas, PLLC

(57) ABSTRACT

The present invention provides a method for microelectronic positioning bioparticles, which utilizes dielectric and non-contact electrical force of cell themselves associated with multi-phase electrical signals to attain uniformity of distribution of the bioparticles and positioning thereof within micro-areas in a cell culture system. The obstacle of system geometrical structure is eliminated so as to simplify the system layout and programmably change cells' positions. The present method is suitable for treating cell array in a large quantity. The present method utilizes electrical control for the cells. The clamping of the cells can be removed at any time. It is very advantageous for collection and redistribution of cell products.

5 Claims, 6 Drawing Sheets

MICROELECTRONIC POSITIONING FOR BIOPARTICLES

BACKGROUND OF THE INVENTION

1. Field of the Invention

The present invention relates to a method for positioning bioparticles, and more particularly to a method for controlling distribution and positions of the bioparticles with multi-phase electrical signals.

2. Description of the Related Art

In a vessel culture system, cells can obtain fresh nutrient supply from liquid medium; the way to make cells positioning and distribution uniformly becomes a major issue. Referring to FIG. 1, U.S. Pat. No. 6,653,124 discloses a vessel cell culture system. The vessel cell culture system has a plurality of individual arrayed cell culture rooms 1, and each cell culture room 1 has its own nutrient supply micro-channels 11. Although each cell culture room 1 disclosed in U.S. Pat. No. 6,653,124 can control nurturing environment individually, but it still has problems about dead places from sluggish floating medium, unbalanced nutrient supply, and cell deformation from extruding.

Referring to FIG. 2, a method for fixing cells 22 onto a biochip 20 with soft lithography is disclosed by Park T. H., and others, in Biotechnol. Prog. 2003, 19, 243-253. First, a stencil 21 with a micro-hole array structure is placed on the biochip 21. After the cell suspension is fastened in the openings formed of the micro-hole array structure of the stencil 21, the stencil 21 is removed to form a cell micro-array chip. Although the method can precisely position a group of cells in the openings, but can not control the uniformity of distribution of the cells.

U.S. Pat. No. 5,795,457 discloses a way to use dielectrophoresis (DEP) theorem to catch cells. Referring to FIG. 3, AC signals are applied unto adjacent castled electrodes 31, 32, and then under different AC frequencies, two different dielectric cells 35, 36 are caught and separated to different regions. The method disclosed in U.S. Pat. No. 5,795,457 uses non-mechanical and non-contact force to position cells, but it can not confirm uniformity of the cell distribution. Furthermore, a method for catching cells with DEP theorem is disclosed by Ozkan M. and others, in Langmuir 2003, 19, 1532-1538. The method adds AC signals to upper and lower electrodes to catch cells and position the cells on electrode array. But this method also can not confirm uniformity of the cell distribution.

SUMMARY OF THE INVENTION

One objective of the present invention is to provide a method for positioning bioparticles, which utilizes dielectric and non-contact electrical force of cell themselves associated with multi-phase electric signals to attain uniformity of cell distribution and nutrient supply in a cell culture system.

It is another objective of the present invention to provide a method for positioning bioparticles, which is suitable for large-scale cell culture.

It is another objective of the present invention to provide a method for positioning bioparticles, which can programmably change cell's position and remove cell's clamping at any time so that it is very advantageous for collection and redistribution of cell products.

According to these above objectives, the present invention provides a method for positioning bioparticles, which comprises providing a cell culture system provided with an electrode array therein where the electrode array has a plurality of electrodes; introducing a liquid containing bioparticles into the cell culture system; and simultaneously applying several AC signals unto the electrode array, wherein the AC signals have different phases but the same voltage and frequency so as to let the bioparticles position in predetermined regions by electric forces.

In another aspect, the present invention provides a method for controlling uniform distribution of bioparticles, which comprises providing a cell culture system with an electrode array provided therein, where the electrode array includes several electrode groups and each electrode group has a plurality of adjacent electrodes; introducing a liquid containing bioparticles in the cell culture system; and simultaneously applying a plurality of AC signals unto each of the electrode groups, wherein each of the AC signals is added unto one electrode of the electrode group to make the two AC signals applied unto each two adjacent electrodes have the same voltage and the same frequency but have different phases, so that the bioparticles can position uniformly with electric forces.

DETAILED DESCRIPTION OF THE PREFERRED EMBODIMENTS

Figure 1:
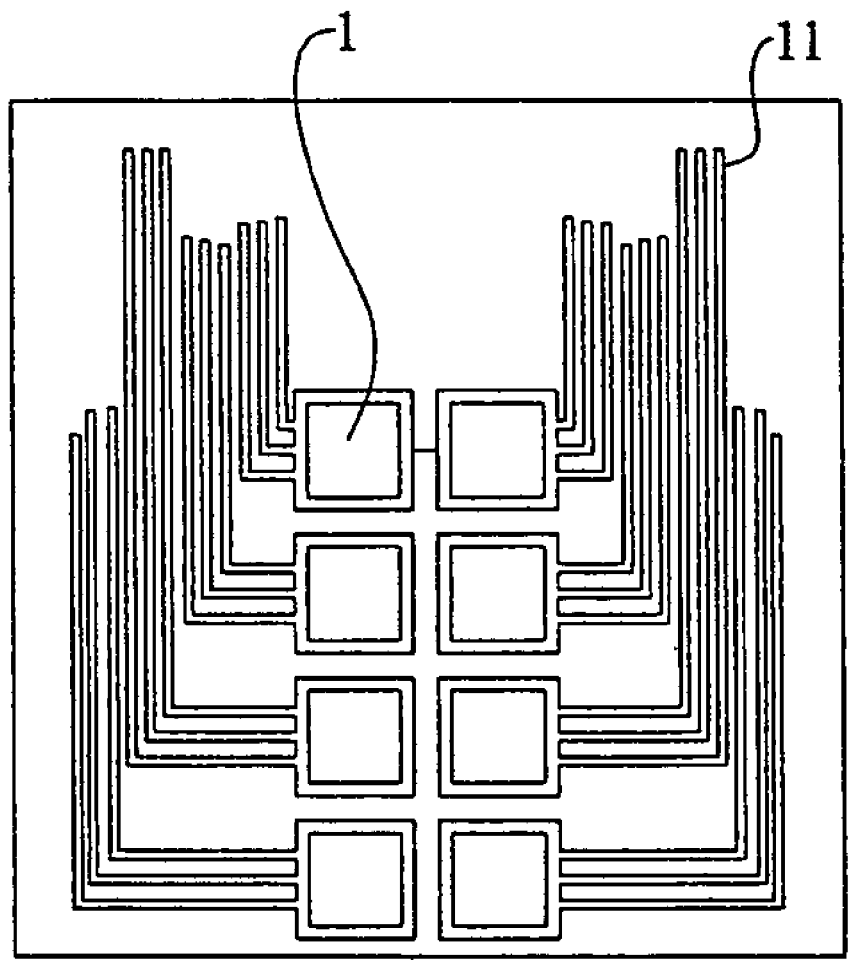
FIG. 1 shows diagrammatically a traditional arrayed vessel cell culture system.
Figure 2:
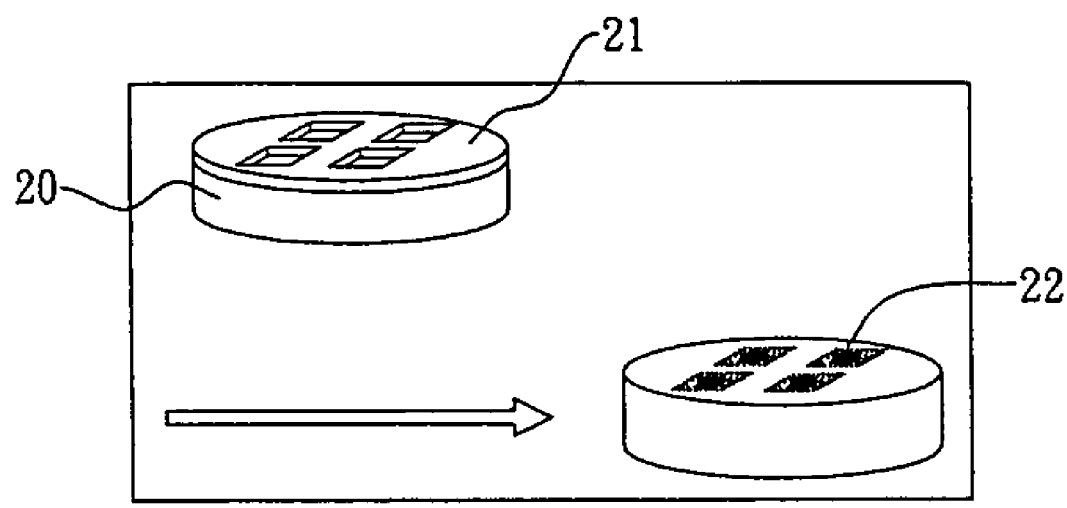
FIG. 2 shows diagrammatically a step mapping of a traditional bioparticle array chip.
Figure 3:
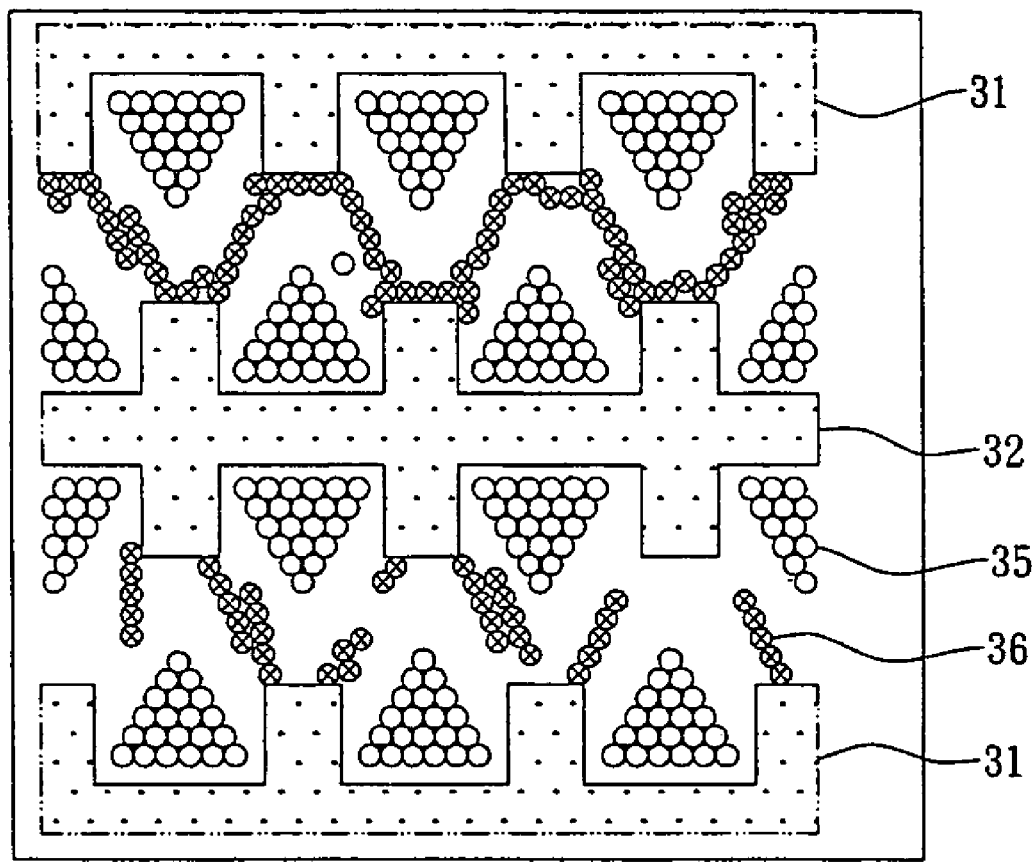
FIG. 3 shows diagrammatically a situation that the traditional castled electrode array catches cells.

The present invention provides a method for microelectronic positioning bioparticles, which utilizes non-constructive and non-contact electrical control for bioparticles' positioning and distribution to avoid a complex structure layout of the cell culture system. As such, the present invention can avoid non-uniform of cell distribution and cell deformation from extruding of the system structure. The working principle of the present invention will be described in the following:

Due to different dielectric properties, dielectric particles and their surrounding medium bring different polarization capability under un-uniform electric fields. The polarization of the particles which are likely to electric dipolar interacts with the electric field to generate force called dielectrophoresis (DEP). The formula is written as followed:

$$<F(t)>=2\pi \in_m r^3 (Re[f_{CM}]\nabla E^2_{rms} + Im[f_{CM}](E^2_{x0}\nabla \phi_x + E^2_{y0}\nabla \phi_y + E^2_{z0}\nabla \phi_z)) \quad (1)$$

which $f_{CM}$ is Clausius Mossotti factor, and is related to frequencies and dielectric coefficients of the particles and solution. The present invention uses parameters which can affect DEP to make different signal sources applied unto electrodes. Traditionally, positive DEP and negative DEP directly apply signals from the signal generator unto the electrodes, therefore only the first term of the right side of formula (1) comes to work. The present invention adds phase-variation electric signal to bring the second term of the right side of the formula (1) to work. Under adjustment of the proper parameters, the present invention can change the particles' gathering position at the same frequency by adjusting the phase of input signals. The traditional positive DEP and negative DEP use different frequencies for adjustment.

As to enable uniformity of the cell distribution, the present invention adjusts system parameters to let the particles reach maximum disorder vibration under the electric field distribution generated from non-uniform DEP. The first term of the right side of the formula (1) can attract the particles to the electrodes or push them away from electrodes, and when the electric field is large, convention will happened. The convention is regional and always happened in the place where it has low frequency and dense electric lines. When simultaneously adding multi-phase signals, i.e. adding the contribution of the second term of the formula (1) and under adjustment of proper parameters, the regional convection becomes more complicated, and the particles will have maximum disorder vibration. According to this disorder vibration, the system can reach uniform cell distribution.

In brief, the present invention provides a method for microelectronic positioning bioparticles, which utilizes dielectric and non-contact electrical force of the cells themselves associated with multi-phase electrical signals to attain uniformity of distribution of the bioparticles and positioning thereof within micro-areas in the cell culture system. The system layout is simplified, and it can programmably change cells' positions. The present method is suitable for treating cell array in a large quantity. The present method utilizes electrical control for the cells. The clamping of the cells can be removed at any time. It is very advantageous for collection and redistribution of cell products.

The present invention will be described in detail by way of following examples and accompanying drawings. Latex particles are used in these examples to emulate experiments to prove the efficiency of the present invention for dielectric particles' positioning by electrical force and uniform distribution of the dielectric particles.

FIRST EXAMPLE

Figure 4:
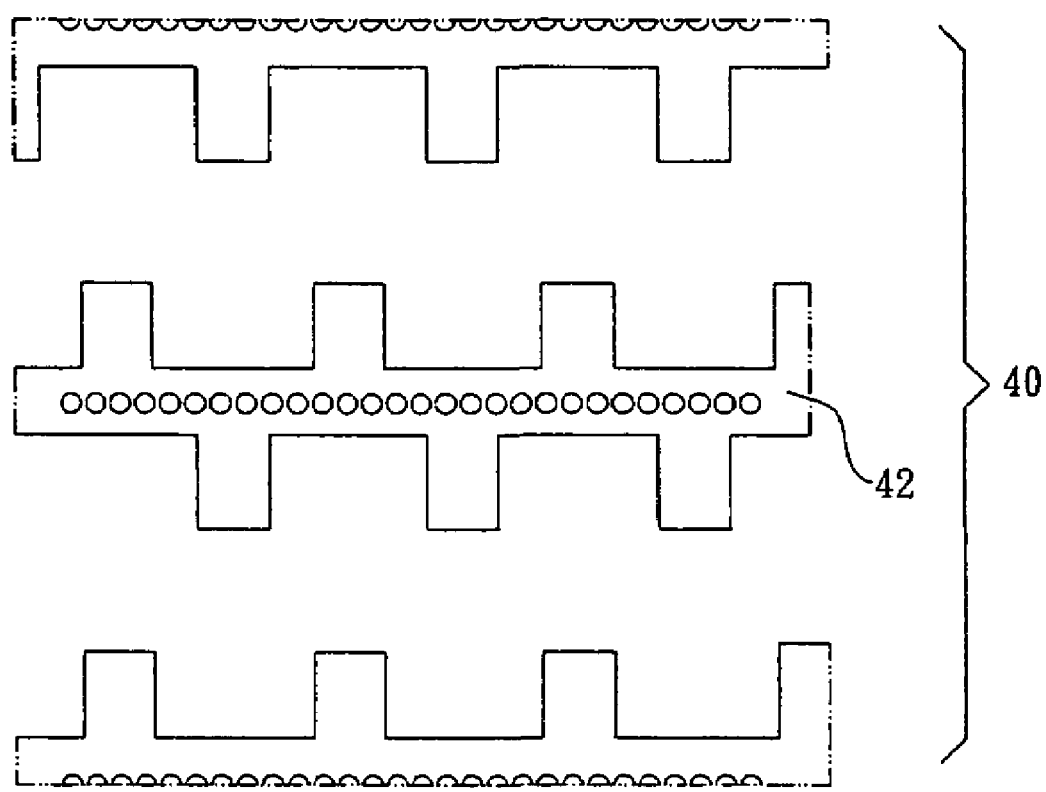
FIG. 4 shows the first situation that the electrode array of the present invention gathers latex particles.

In the first example, an electrode array 40 is set on an inner sidewall of a vessel cell culture system (not shown). The electrode array 40 is composed of a plurality of parallel interdigitated castellated electrodes 42. First, the latex particle solution is introduced into the vessel cell culture system, and then the adjacent interdigitated castellated electrodes 42 are applied with the first AC signal with 0 degree phase and the second AC signal with 180 degree phase individually. The first AC signal and the second AC signal are both have 20 KHz frequency and 14 Vpp voltage, and the conductivity of the latex particle solution is $1\times10^{-4}$ S/m. Referring to FIG. 4, the latex particles will gather on the central portion of the interdigitated castellated electrodes.

SECOND EXAMPLE

Figure 5:
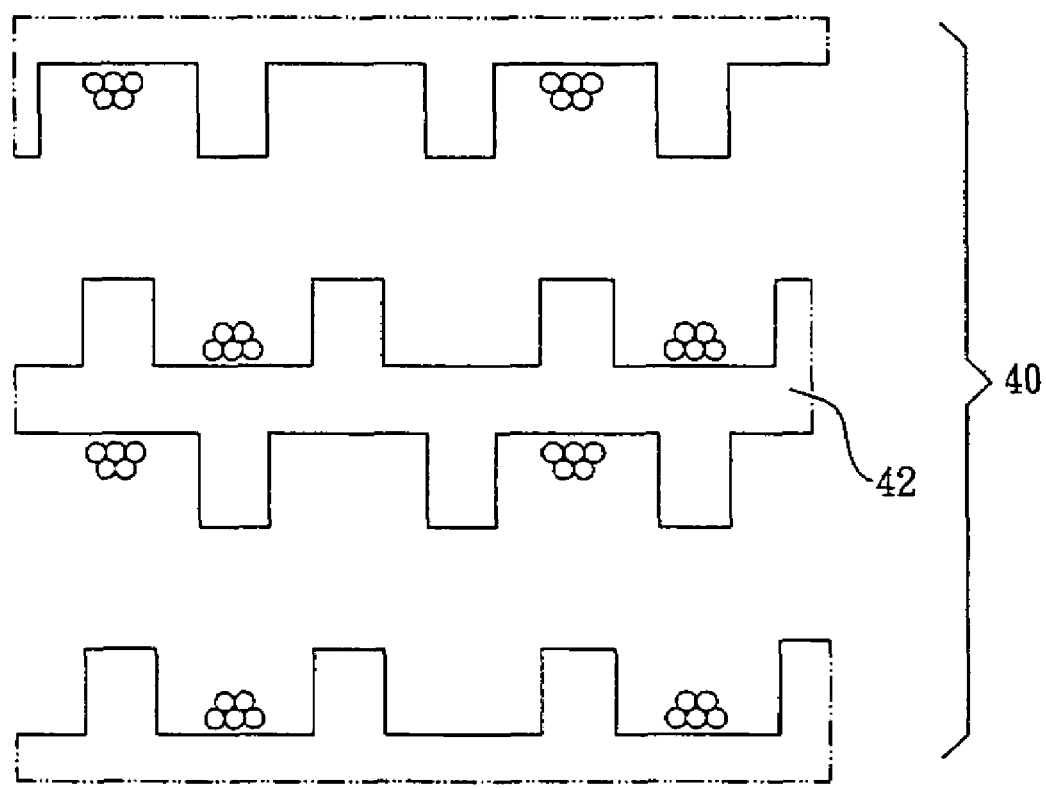
FIG. 5 shows the second situation that the electrode array of the present invention gathers latex particles.

Different from the first example, the second example changes the phase of the second AC signal to 90 degree. As such, the adjacent interdigitated castellated electrodes 42 are applied with the first AC signal with 0 degree phase and the second AC signal with 90 degree phase. The first AC signal and the second AC signal are both have 20 KHz frequency and 20 Vpp voltage, and the conductivity of the latex particle solution is $1\times10^{-4}$ S/m. Referring to FIG. 5, the result reveals that the latex particles gather in the space between the adjacent teeth-like electrodes of the same interdigitated castellated electrode 42, and the latex particles periodically gather in the space without electrodes.

According to the above examples, the present invention can apply AC signals with different phases unto adjacent electrodes individually. As such, the latex particles can gather in particular regions so as to reach electric positioning.

THIRD EXAMPLE

Figure 6:
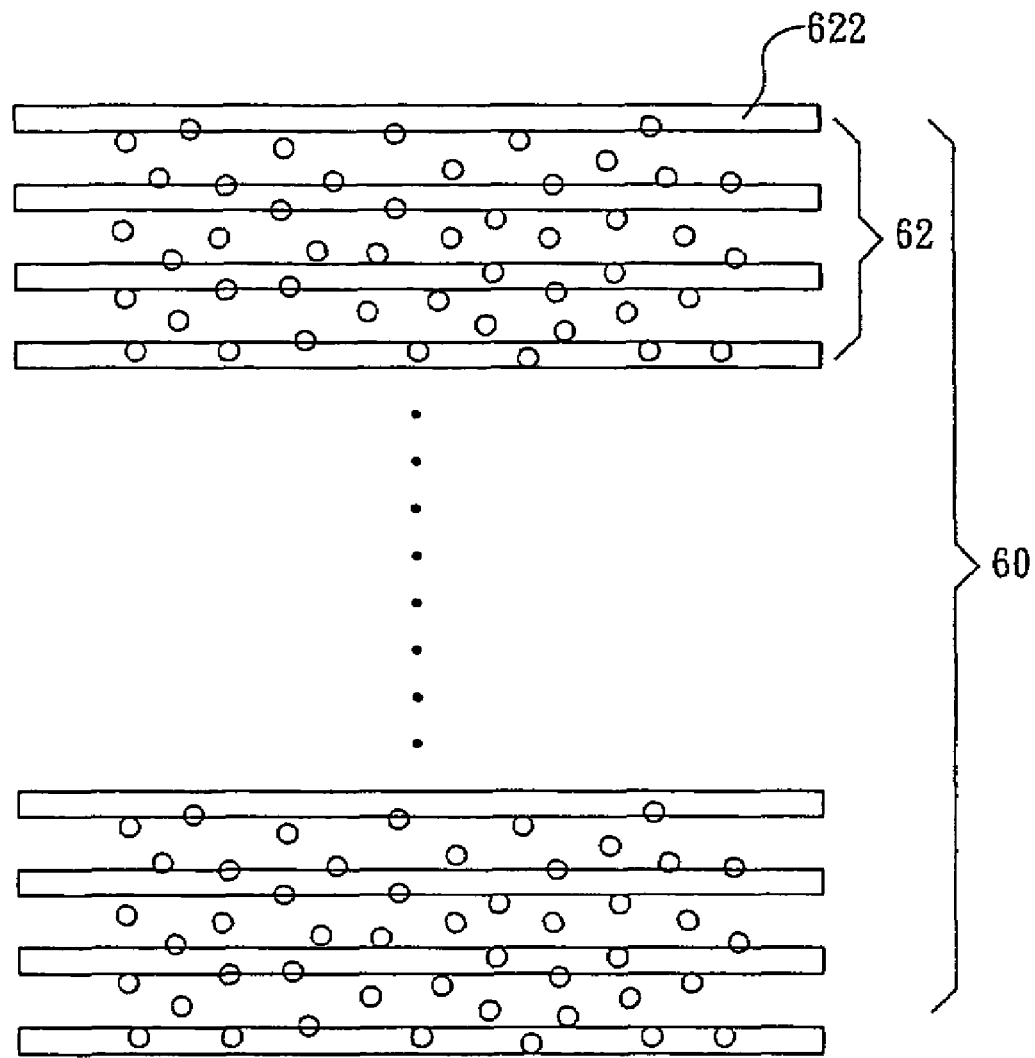
FIG. 6 shows the third situation that the electrode array of the present invention gathers latex particles.

In the third example, an electrode array 60 is set on an inner sidewall of the vessel cell culture system. The electrode array 60 is divided to a plurality of electrode groups 62, and each electrode group 62 has four adjacent electrodes 622. Four AC signals with 0 degree, 90 degree, 180 degree and 90 degree phase are individually applied unto one of the four adjacent electrodes 622 of each electrode group 62 so that each of the adjacent electrodes 622 has the AC signal with different phase applied thereupon. Each electrode 622 has 24 KHz frequency and 18 Vpp Voltage, and the conductivity of the latex particle solution is $1\times10^{-4}$ S/m. Referring to FIG. 6, under such the circumstance, the latex particles produce violent vibrations, and thus the latex particles uniformly distribute.

While the invention has been described by way of examples and in terms of preferred embodiments, it is to be understood that those who are familiar with the subject art can carry out various modifications and similar arrangements and procedures described in the present invention and also achieve the effectiveness of the present invention. Hence, it is to be understood that the description of the present invention should be accorded with the broadest interpretation to those who are familiar with the subject art, and the invention is not limited thereto.

What is claimed is:

1. A method for controlling uniform distribution of dielectric particles, comprising:
    providing a cell culture system structure with an electrode array provided therein, said electrode array having several electrode groups and each of said electrode groups having a plurality of adjacent electrodes;
    introducing a liquid containing dielectric particles into said cell culture system; and
    simultaneously applying a plurality of AC signals unto each said electrode group, wherein each said AC signal is individually applied onto one of said electrodes in said electrode group, and each said two adjacent electrodes have AC signals with different phases but the same voltage and frequency so as to let said particles be uniformly distributed by electric forces.

2. The method for controlling uniform distribution of dielectric particles as claimed in claim 1, wherein said AC signals of said two adjacent electrodes have 90 degree phase difference.

3. The method for controlling uniform distribution of dielectric particles as claimed in claim 1 wherein the dielectric particles are cells.

4. The method for controlling uniform distribution of dielectric particles as claimed in claim 1, wherein a dielectropphoroesis force is developed by interaction of said electric field and said dielectric particles.

5. The method for controlling uniform distribution of dielectric particles as claimed in claim 1, wherein said cell culture system structure is a vessel culture system structure.

* * * * *